US006387381B2

(12) United States Patent
Christensen

(10) Patent No.: US 6,387,381 B2
(45) Date of Patent: *May 14, 2002

(54) SEMI-MOIST ORAL DELIVERY SYSTEM

(75) Inventor: Edwin H. Christensen, Coral Springs, FL (US)

(73) Assignee: EZ-Med Company, Pompano Beach, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 49 days.

(21) Appl. No.: 09/160,618

(22) Filed: Sep. 24, 1998

(51) Int. Cl.$^7$ .......................... A61K 9/00; A61K 47/00; A61K 9/68; A23K 1/17; A23L 1/30
(52) U.S. Cl. .................... 424/400; 424/439; 424/440; 424/441; 424/442; 424/484; 426/72
(58) Field of Search ............................... 424/439, 441, 424/442, 484, 400, 440; 426/72

(56) References Cited

U.S. PATENT DOCUMENTS

| 3,567,819 A | | 3/1971 | Idson et al. |
| 3,615,652 A | | 10/1971 | Burgess et al. |
| 4,025,624 A | * | 5/1977 | Alphin et al. ................ 424/233 |
| 4,284,652 A | | 8/1981 | Christensen |
| 4,327,076 A | | 4/1982 | Puglia et al. |
| 4,643,908 A | | 2/1987 | Sawhill |
| 4,671,953 A | | 6/1987 | Stanley et al. |
| 4,710,387 A | | 12/1987 | Uiterwaal et al. |
| 4,795,643 A | * | 1/1989 | Seth ............................ 424/456 |
| 4,882,153 A | * | 11/1989 | Yang et al. .................. 424/440 |
| 4,935,243 A | * | 6/1990 | Borkan et al. ............... 424/441 |
| 5,262,167 A | | 11/1993 | Vegesna et al. |
| 5,296,209 A | | 3/1994 | Simone et al. |
| 5,456,922 A | | 10/1995 | Cady et al. |
| 5,637,313 A | | 6/1997 | Chau et al. |
| 5,643,603 A | | 7/1997 | Bottenberg et al. |

* cited by examiner

Primary Examiner—Thurman K. Page
Assistant Examiner—Todd D Ware
(74) Attorney, Agent, or Firm—Welsh & Katz, Ltd.

(57) ABSTRACT

The subject invention is a carrier or product formed of a matrix having starch, sugar, fat, polyhydric alcohol and water in suitable ratios such that there exists a water activity of 0.6–0.75. The water activity of the product matrix may be adjusted up or down so that the availability of water in the finished product is not detrimental to the included active ingredient, be it pharmaceutical, nutraceutical, or a vitamin mineral complex.

23 Claims, No Drawings

SEMI-MOIST ORAL DELIVERY SYSTEM

FIELD OF THE INVENTION

This application is directed to a means for delivering pharmaceuticals, nutraceuticals and the like to a mammal and more specifically, the control of the water activity of a food product matrix for use in the incorporation of a pharmaceutical, nutraceutical or other bioactive compound into the matrix.

BACKGROUND OF THE INVENTION

Pharmaceutical and nutraceutical products intended for oral administration are typically provided in tablet, capsule, pill, lozenges and caplet form. These products are swallowed whole or chewed in the mouth for delivery of the active ingredient into the alimentary system of a body. Such oral delivery systems are sometimes made chewable to ease drug administration in pediatric and geriatric patients. Such concerns with ease of administration may be amplified when dealing with pets and other animals.

As a result, several approaches have been utilized in formulating oral delivery systems, including gums and candy bases. The use of such delivery systems is limited by the reaction of the active ingredient, whether it be pharmaceutical, nutraceutical or other ingredients, to the existence of water in the system.

SUMMARY OF THE INVENTION

Therefore, an object of the subject invention is a method of controlling water activity in an oral delivery system and the product thereof.

These and other objects are attained by the subject invention wherein there is provided a carrier or product formed of a matrix having starch, sugar, fat, polyhydric alcohol and water in suitable ratios such that there exists a water activity of 0.6–0.75. The water activity of the product matrix is adjusted up or down so that the availability of water in the finished product is not detrimental to the included active ingredient, be it pharmaceutical, nutraceutical, or vitamin mineral complex.

A further object of the subject invention is a oral delivery system for pharmaceuticals, nutraceuticals or other active ingredient which matches the water activity of the carrier to the included active ingredient.

DESCRIPTION OF THE PREFERRED EMBODIMENTS

By the subject invention, a soft chewable oral delivery system is provided. The dosage form may be in tablet form and may contain one or more active ingredients. The active ingredients are incorporated into the system which is described in further detail below and which includes a starch component, a fat or oil, a sugar component, a polyhydric alcohol, water and other minor ingredients. Into this mixture is placed the active ingredient. After mixing and extruding these ingredients, the extrudate is formed into the appropriate shape. The relative proportions of the mixture are as follows.

| | |
|---|---|
| Starch | 10–50% |
| Fat or Oil | 0–40% |
| Sugar | 5–25% |
| Polyhydric Alcohol | 10–50% |
| Water | 5–20% |
| Salt (NaCl) | 1–5% |
| Active Ingredient | 0.1–5% |

Generally speaking, the starch component of the matrix comprises 10 to 50 percent by weight of the matrix. More particularly, the starch component of the matrix comprises 15 to 40 percent by weight of the matrix.

While starch for use in the matrix can be of any suitable type, it is most preferred that at least part of the starch in the matrix be a highly derivatized or pregelatinized starch. If a highly derivatized starch is present in the matrix, it should be present in an amount of about ½ percent by weight of the total starch and the balance of the starch being non-derivatized. More preferably, about 20–40 percent by weight of the total matrix and about 45% of the total starch should be the derivatized starch. An example of a preferred pregelatinized starch is A. E. Staley's NU-COL 4227 or SOFT-SET.

Other amylaceous ingredients may be used in combination with the derivatized starch or alone, provided the starch limits are not exceeded. The amylaceous ingredients can be gelatinized or cooked before or during the forming step to achieve the desired matrix characteristics. If gelatinized starch is used, it may be possible to prepare the product of the subject invention or perform the method of the subject invention without heating or cooking of any sort. However, if ungelatinized (ungelled) or uncooked starch is used, the matrix must be cooked sufficiently to gel or cook the starch to reach the desired content.

Starches that can serve as a base starch for derivatization include regular corn, waxy corn, potato, tapioca, rice, etc. Such types of derivatizing agents for the starch include but are not limited to ethylene oxide, propylene oxide, acetic anhydride, and succinic anhydride, and other food approved esters or ethers, introducing such chemicals alone or in combination with one another. Prior crosslinking of the starch may or may not be necessary based on the pH of the system and the temperature used to form the product.

By "amylaceous ingredients" is meant those food-stuffs containing a preponderance of starch and/or starch-like material. Examples of amylaceous ingredients are cereal grains and meals or flours obtained upon grinding cereal grains such as corn, oats, wheat, milo, barley, rice, and the various milling by-products of these cereal grains such as wheat feed flour, wheat middlings, mixed feed, wheat shorts, wheat red dog, oat groats, hominy feed, and other such material. Also included as sources of amylaceous ingredients are the tuberous food stuffs such as potatoes, tapioca, and the like.

Another component of the matrix is a fat component such as fat or oil of animal or vegetable origin. Typical animal fats or oils are fish oil, chicken fat, tallow, choice white grease, prime steam lard and mixtures thereof. Other animal fats are also suitable for use in the matrix. Vegetable fats or oils are derived from corn, soy, cottonseed, peanut, flax, rapeseed, sunflower, other oil bearing vegetable seeds, and mixtures thereof. Additionally, a mixture of animal or vegetable oils or fats is suitable for use in the matrix. The fat component of the matrix is about 0 to about 40% by weight of the matrix. More specifically, the fat component of the matrix is about 20 percent by weight of the matrix.

The polyhydric alcohol component of the matrix can be selected from glycerol, sorbitol, propylene glycol, 1,3- butanediol, and mixtures thereof with each other and other polyhydric alcohols. Generally the polyhydric alcohol comprises about 10 to about 50 percent by weight of the matrix. More specifically, the polyhydric alcohol comprises about 20 to about 40 percent by weight of the matrix.

The sugar component can be employed in a dry or crystalline condition or can be an aqueous syrup having a sugar concentration of from 50 to about 95, preferably from 70 to about 80, weight percent. The sugar used can be lactose, sucrose, fructose, glucose, or maltose, depending on the particular application and price or availability of a particular sugar. Examples of various well established sources of these sugars are, corn syrup solids, malt syrup, hydrolyzed corn starch, hydrol (syrup from glucose manufacturing operations), raw and refined cane and beet sugars, etc.

Water must be present in the matrix at least about 5 percent by weight of the matrix. More specifically, water is present in the matrix about 5 percent to about 20 percent by weight of the matrix. The matrix thus formed usually has a water activity of 0.60 to 0.75.

While water must be at least 5 percent by weight of the matrix, when the matrix is used in a food product, the moisture of the food product must be adjusted. Generally the moisture content of the matrix is such to give a moisture content of 5–15 percent to the final soft dry food product. More preferred is a moisture content of 5 percent to 14 percent. Most preferred is a moisture content of 8 percent to 13 percent. The desired moisture content may be achieved in any suitable fashion. Normal processing may produce the moisture content desired. A standard drying step is optional and may be used if necessary.

The active ingredient may be any drug, nutrition agent, or the like which can be orally administered. Exemplary of such active ingredients are the following: nutraceuticals, such as chromium picolinate, potassium gluconate and methionine amino acid; prescription drugs, such as ivermectin, fenbendazole, piperazine, magnesium hydroxide, stranozole, furosemide, penicillin, amoxicillin, prednisolone, methylprednisolone, acepromazine; and, other pharmaceutical products, such as aspirin, prozac, zantac, and benedryl. Minor amounts of flavorants, colorants, glycerin, flavor enhancers, sweeteners, emulsifiers, antibitterness agents, taste masking agents, stabilizers, preservatives, or combinations thereof may be added.

To form the matrix, the starch system, fat, polyhydric alcohol, corn syrup and water are mixed with a screw extruder, permitting addition of ingredients and variable heating at different points along the barrel. Other mixing apparatus, such as a sigma mixer, swept wall heat exchanger or the like may be used. If a coloration is desired in the final product, cooked or pregelled starches are used to form the matrix. The use of these starches avoids high cooking temperatures which would destroy the desired coloration and/or active ingredient. If coloration active temperature sensitivity is not a problem, it is possible to use an uncooked or ungelatinized starch to form the matrix and cook or gel the starch as the process is carried out. The incorporation of a derivatized starch in the product more clearly guarantees the softness of the product for a longer period of time. Softness is also provided by the fats and oils. In this fashion a suitable matrix is provided for use with a wide variety of active ingredients.

Having fully described the invention, the following examples are presented to illustrate the invention without limitation thereof. In these examples all parts percentages are by weight unless otherwise specified.

EXAMPLE 1

Carrier

| INGREDIENT | PARTS |
|---|---|
| Regular Corn Starch (Purefood GMI) | 18.0 |
| Pregel Starch (SOFT SET) | 15.0 |
| Corn Syrup (Star Dri Corn Syrup Solids) | 15.0 |
| Corn Oil | 20.0 |
| Sorbitol | 20.0 |
| $H_2O$ | 10.0 |
| Salt | 2.0 |
| TOTAL | 100.0 |

The above ingredients are mixed at temperatures of about 125° F., extruded and cut into a suitable tablet size. This product has an oily, bubbly appearance suggesting cutting back on the oil content. Temperature was also adjusted during each of the following examples to eliminate puffing of the product as it exits the extruder.

EXAMPLE 2

Guaifenesin

| INGREDIENT | PARTS |
|---|---|
| Regular Corn Starch (Purefood GMI) | 17.9 |
| Pregel Starch (SOFT SET) | 15.0 |
| Corn Syrup (Star Dri Corn Syrup Solids) | 15.0 |
| Sorbitol | 39.3 |
| $H_2O$ | 10.0 |
| Salt | 2.0 |
| Guaifenesin* | 0.8 |
| TOTAL | 100.0 |

*Available from Arrow Chemical Co., N.J.

EXAMPLE 3

Vitamins

| INGREDIENT | PARTS |
|---|---|
| Regular Corn Starch (Purefood GMI) | 17.9 |
| Pregel Starch (SOFT SET) | 15.0 |
| Corn Syrup (Star Dri Corn Syrup Solids) | 15.0 |
| Sorbitol | 35.1 |
| $H_2O$ | 10.0 |
| Salt | 2.0 |
| Vitamin and Mineral Mix* | 5.0 |
| TOTAL | 100.0 |

*Commercially available mixture available from Archer Daniels Midland.

EXAMPLE 4

Flax

| INGREDIENT | PARTS |
| --- | --- |
| Regular Corn Starch (Purefood GMI) | 17.9 |
| Pregel Starch (SOFT SET) | 15.0 |
| Corn Syrup (Star Dri Corn Syrup Solids) | 15.0 |
| Sorbitol | 35.1 |
| H$_2$O | 10.0 |
| Salt | 2.0 |
| Flax* | 5.0 |
| TOTAL | 100.0 |

*Available from Enreco Flax.

EXAMPLE 5

Acetaminophen

| INGREDIENT | PERCENT |
| --- | --- |
| Regular Corn Starch (Purefood GMI) | 17.9 |
| Pregel Starch (SOFT SET) | 15.0 |
| Corn Syrup (Star Dri Corn Syrup Solids) | 15.0 |
| Sorbitol | 39.1 |
| H$_2$O | 10.0 |
| Salt | 2.0 |
| Acetaminophen* | 0.8 |
| Red Coloring #40 | 0.1 |
| Flavoring (Cherry) | 0.1 |
| TOTAL | 100.0 |

*Available from Mallincrodt as Compap

EXAMPLE 6

Carrier

| INGREDIENT | PARTS |
| --- | --- |
| Regular Corn Starch (Purefood GMI) | 17.9 |
| Pregel Starch (SOFT SET) | 15.0 |
| Corn Syrup (Star Dri Corn Syrup Solids) | 15.0 |
| Sorbitol | 40.1 |
| H$_2$O | 10.0 |
| Salt | 2.0 |
| TOTAL | 100.0 |

TABLE 1

| Example | Active | Oil/Sugar | A$_w$ | Extrusion Temp. |
| --- | --- | --- | --- | --- |
| 1 | Premix | Corn Oil/Sorbitol | N/A | 125 |
| 2 | Guaifenesin | 100% Sorbitol | 0.656 | 115 |
| 3 | Vitamin Mix | 100% Sorbitol | 0.651 | 115 |
| 4 | Flax | 100% Sorbitol | 0.673 | 115 |
| 5 | Acetaminophen | 100% Sorbitol | 0.666 | 115 |
| 6 | Premix | 100% Sorbitol | 0.61 | 115 |

By the above examples and Table 1 it is apparent that an oral delivery system for the administration for pharmaceuticals, nutraceuticals, vitamins and minerals and other active ingredients may be provided in a chewable form by the subject invention. If the active ingredient is water sensitive such as aspirin, then the amount of polyhydric alcohol is increased, the water activity is depressed to about 0.65 and the stability and texture of the resultant product is maintained. If the active ingredient requires or can tolerate the presence of free water for its activity, such as in the case of Guaifenesin, the amount of polyhydric alcohol may be decreased, while maintaining the level of such polyhydric alcohol such that a soft texture of the resulting tablet is maintained. In the case of Guaifenesin, then an A$_w$ of 0.70 may be utilized and a softer, more chewable texture achieved. An effective oral delivery system in which the texture and stability of the product and activity of the active ingredient is controllable, is the result.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

Various features of the invention are set forth in the following claims.

What is claimed is:

1. A composition for the oral administration of an additive selected from the group consisting of pharmaceutical, nutritional supplements, vitamins and minerals, and mixtures thereof mammals in a discrete dosage form, said discrete dosage from comprising:

said additive, an extrudate comprising a matrix having about 10 to about 50% wt starch, a sweetener consisting essentially of sucrose, corn syrup and sorbitol, said sucrose being in an amount of at least 10%, and at least about 5% wt water, said composition having A$_w$ of about 0.60 to about 0.75, and a soft and chewy texture, and said A$_w$ being adjusted to permit an appropriate amount of free water in the presence of the additive.

2. The carrier of claim 1 wherein the water content is about 10%.

3. The carrier of claim 1 wherein the polyhydric alcohol content is about 40%.

4. The carrier of claim 1 wherein the starch content is about 32%.

5. The carrier of claim 1 wherein said carrier has a pregelatinized starch content of about 15%.

6. The carrier of claim 1 where the A$_w$ is 0.65 and the additive is aspirin.

7. The carrier of claim 1 wherein the polyhydric alcohol is sorbitol.

8. The carrier of claim 1 wherein the sugar content is about 15%.

9. A method of making a carrier and additive mixture for use in an oral administration of a therapeutically effective amount of the additive in a discrete dosage form, comprising the steps of:

a) forming a matrix and additive admixture by mixing, in a one-step procedure additive,
about 10 to about 50% wt starch,
0 to about 40% wt fat or oil,
a sweetener consisting of sucrose, corn syrup and sorbitol, said sucrose being in an amount of at least 10%,
and water,
and mixing;
adjusting the relative amounts of polyhydric alcohol and water to control the $A_w$ of said admixture to adjust the level of moisture in the carrier to be a level not inimical to the additive and extruding said admixture to form an extrudate.

10. The method of claim 9 including adjusting the water content to about 10%.

11. The method of claim 9 including adjusting the polyhydric alcohol content to about 40%.

12. The method of claim 9 including adjusting the starch content to about 32%.

13. The method of claim 9 including adjusting the sugar content to about 15%.

14. The method of claim 9 further including adding pregelatinized starch to about 15% of the total carrier.

15. The method of claim 9 including the step of mixing in a pharmaceutical.

16. The method of claim 9 including the step of mixing in a nutraceutical.

17. The method of claim 9 including the step of mixing in a vitamin and mineral mix.

18. The method of claim 9 including the step of adding sorbitol.

19. The method of claim 9 including the step of controlling the $A_w$ to be at about 0.60 to about 0.75.

20. The method of claim 9 including the step of adding aspirin as the active ingredient and controlling the $A_w$ of said carrier to about 0.65.

21. The carrier of claim 2, wherein the additive constitutes from about 0.1% to about 5.0% of the resulting mixture.

22. The method of claim 9, further including adding about 0.1% to about 5.0% additive.

23. A composition for the oral administration of a pharmaceutical additive to mammals in a discrete dosage form, said discrete dosage form comprising:

an extrudate having a matrix, and comprising:
10–50% starch,
0–40% fat or oil,
a sweetener consisting essentially of sucrose, corn syrup and sorbitol, said sucrose being in an amount of least 10%,
at least about 5% water, said composition having an $A_w$ of about 0.60 to about 0.75, and a soft and chewy texture, and said $A_w$ being adjusted to permit an appropriate amount of free water in the presence of the additive.

* * * * *